United States Patent
Moll et al.

(10) Patent No.: US 6,391,043 B1
(45) Date of Patent: May 21, 2002

(54) SURGICAL DEVICE WITH SAME TWO CO-OPERATING ELEMENTS FOR GRIPPING AND SEVERING

(75) Inventors: Franciscus Laurens Moll, La Bosch en Duin; Menno Kalmann, Elspeet, both of (NL)

(73) Assignee: Atropos Limited, Dunlin (IE)

( * ) Notice: Subject to any disclaimer, the term of this patent is extended or adjusted under 35 U.S.C. 154(b) by 0 days.

(21) Appl. No.: 09/555,521

(22) PCT Filed: Dec. 9, 1998

(86) PCT No.: PCT/NL98/00708
§ 371 Date: Jul. 14, 2000
§ 102(e) Date: Jul. 14, 2000

(87) PCT Pub. No.: WO99/29238
PCT Pub. Date: Jun. 17, 1999

(30) Foreign Application Priority Data

Dec. 9, 1997 (NL) .............................................. 1007751

(51) Int. Cl.[7] .......................... A61B 17/32; A61B 10/00
(52) U.S. Cl. ...................... 606/174; 606/170; 606/205; 606/207; 30/134
(58) Field of Search ................................ 606/170, 174, 606/205, 207; 600/564; 30/122, 134

(56) References Cited

U.S. PATENT DOCUMENTS

| 5,147,373 | A | | 9/1992 | Ferzli ........................... 606/144 |
| 5,254,129 | A | | 10/1993 | Alexander ................... 606/170 |
| 5,282,826 | A | | 2/1994 | Quadri ........................ 606/207 |
| 5,312,391 | A | | 5/1994 | Wilk .............................. 606/1 |
| 5,893,835 | A | * | 4/1999 | Witt et al. ...................... 601/2 |

FOREIGN PATENT DOCUMENTS

| DE | 3322741 A1 | 1/1985 |
| DE | 4400409 A1 | 7/1995 |
| WO | WO94/05244 | 3/1994 |

* cited by examiner

*Primary Examiner*—Kennedy Schaetzle
*Assistant Examiner*—Kristen Droesch
(74) *Attorney, Agent, or Firm*—Jacobson Holman, PLLC

(57) ABSTRACT

The invention relates to a device for carrying out surgical operations. The device includes a distal part, a middle part extending from the distal part, and a proximal part mounted on the middle part opposite to the distal part. A gripping element of the device is for gripping body tissue and the like. Another element of the device, near the distal part of the device, is for operating the gripping element. Near the distal part of the device is an element for operating a severing component.

9 Claims, 4 Drawing Sheets

SURGICAL DEVICE WITH SAME TWO CO-OPERATING ELEMENTS FOR GRIPPING AND SEVERING

Figure 1:
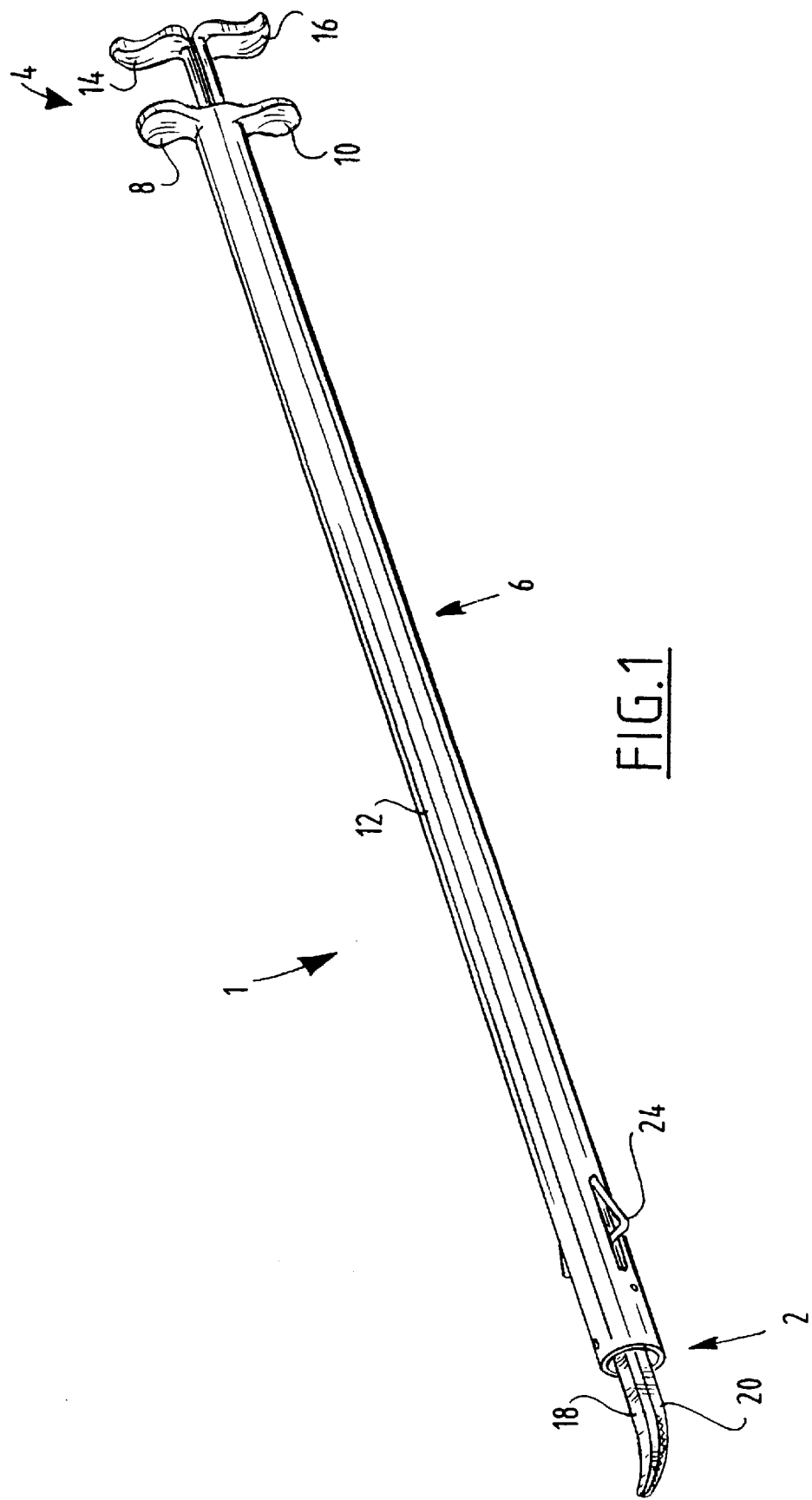

The present invention relates to a surgical device.

Many surgical operations, such as gall bladder operations, are carried out with the aid of an endoscope. The surgeon firstly makes an incision, wherethrough the endoscope is placed into the body. Through another incision, the surgeon brings the surgical instrument into the body in order to carry out the operation. The surgeon can follow the progress of the operation on a screen which provides images from the endoscope. In this manner, vary accurate operations can be carried out.

By many of these types of operations, body tissue has to be removed. In order to remove such body tissue, it is necessary that this is first gripped and secured in place, before the tissue can be severed, whereafter the severed bodily tissue can be removed from the body.

To carry out this process, the surgeon uses a device for gripping and securing in place the body tissue and a second, separate device for severing the tissue. Operating these two instruments simultaneously whilst also operating the endoscope, requires a great deal of surgical skill.

Furthermore, with these sorts of operations, a large incision has to be made in order to accommodate the different surgical instruments at the same time.

An object of the present invention is to obviate one or more of these problems.

The present invention provides an instrument for carrying out one or more surgical operations comprising:
  a distal part;
  a middle part extending from the distal part;
  a proximal part mounted on the middle part opposite to the distal part;
  means for gripping body tissue and the like, which means are mounted near to the proximal part;
  means near the proximal part of the device for severing body tissue and the like;
  means near the distal part of the device for operating the gripping means and means near the distal part of the device for operating the severing means.

The present invention enables a surgeon to grip and sever body tissue without requiring a change of surgical instruments, whereby the problem of relocating the operation position is obviated.

Furthermore, endoscopic operations are facilitated since the surgeon now need only operate one device instead of the previously required two devices whereby only a relatively small incision is required which in turn leads to less trauma and fewer scars for the patient.

The operating means for the gripping and severing means respectively, preferably comprise support means for the gripping and severing means, and the severing means and/or the gripping means are preferably displaceable with respect to each other.

Accordingly the gripping and severing means are independently operable.

The gripping means and severing means preferably comprise the same two co-operating elements, whereby these elements are preferably moveable with respect to each other in a first direction in order to provide a scissor-like severing action, and whereby the elements are preferably moveable with respect to each other in a second direction, in order to grip like a forceps.

In this manner, the two elements can carry out the independent functions of gripping and severing of body tissue, whereby separate gripping and severing instruments are no longer necessary.

According to a second aspect, the present invention provides a method for carrying out a surgical operation utilizing this device.

Figure 2:
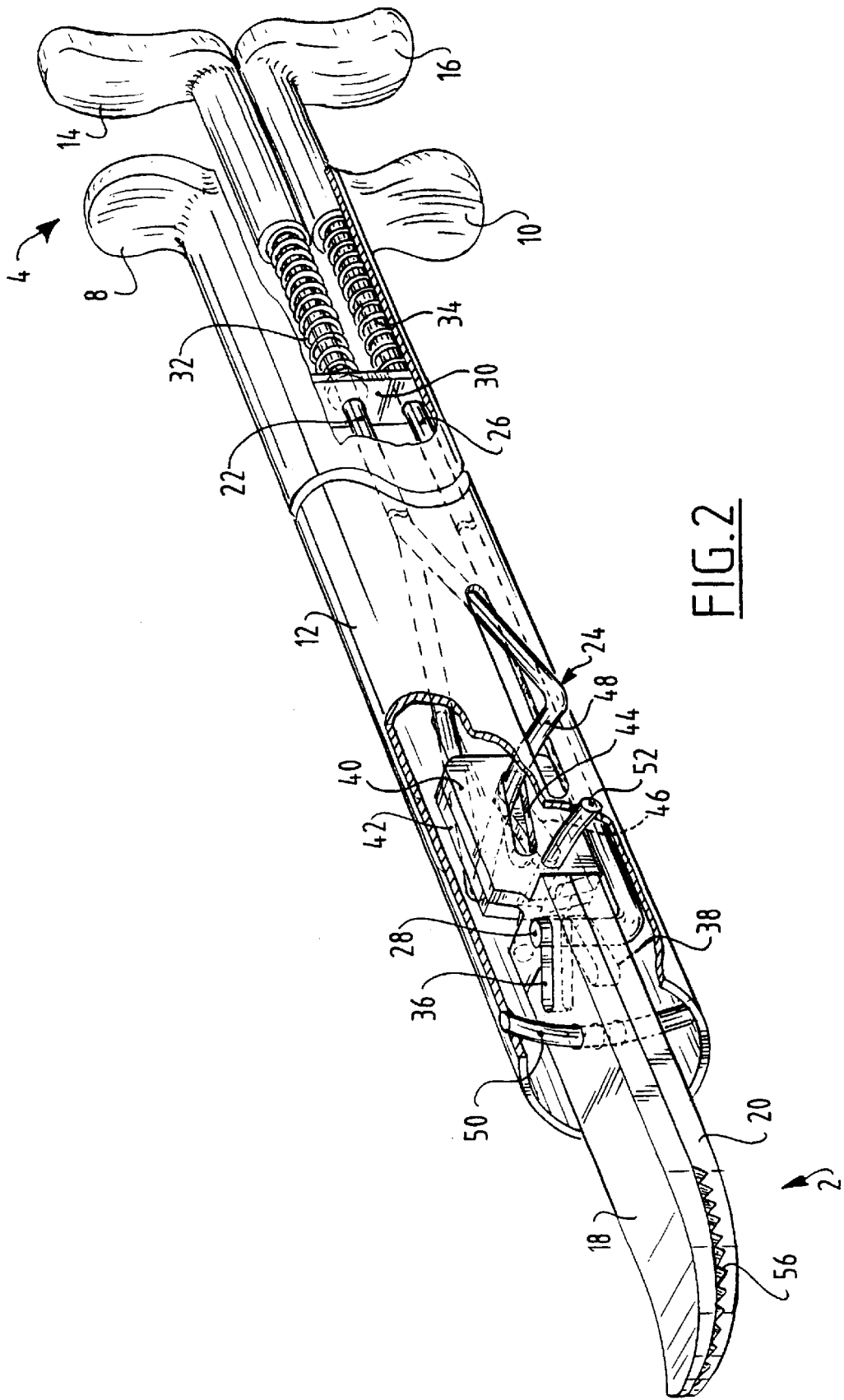
Figure 3:
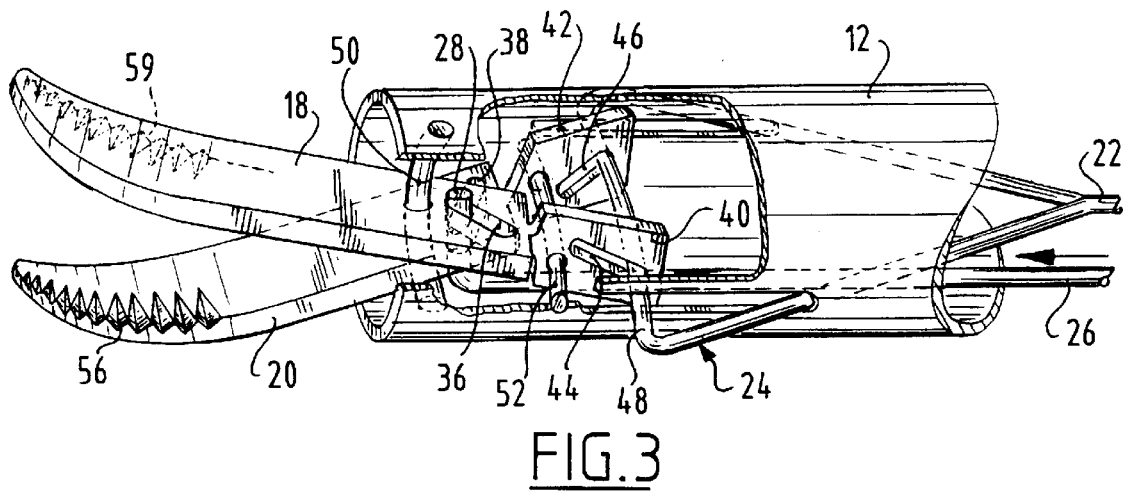
Figure 4:
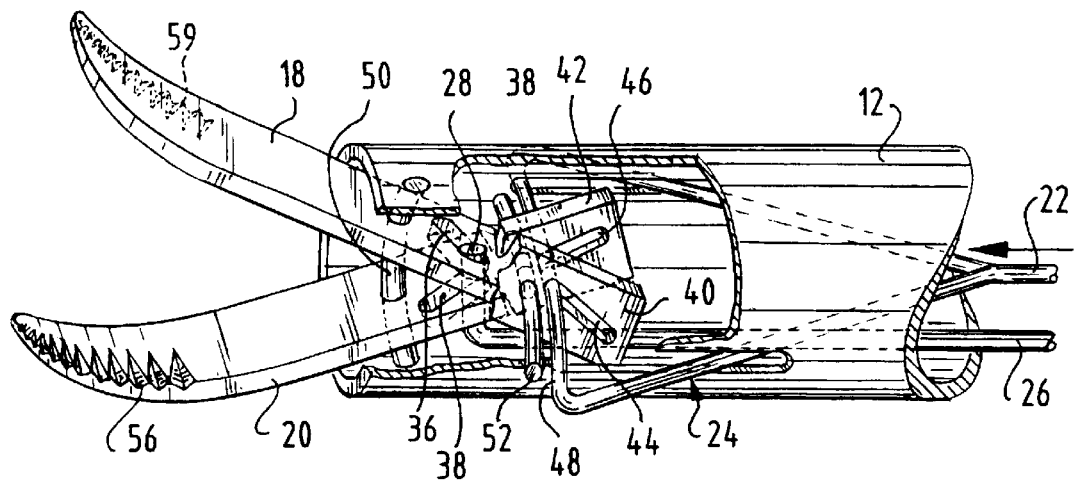
Figure 5:
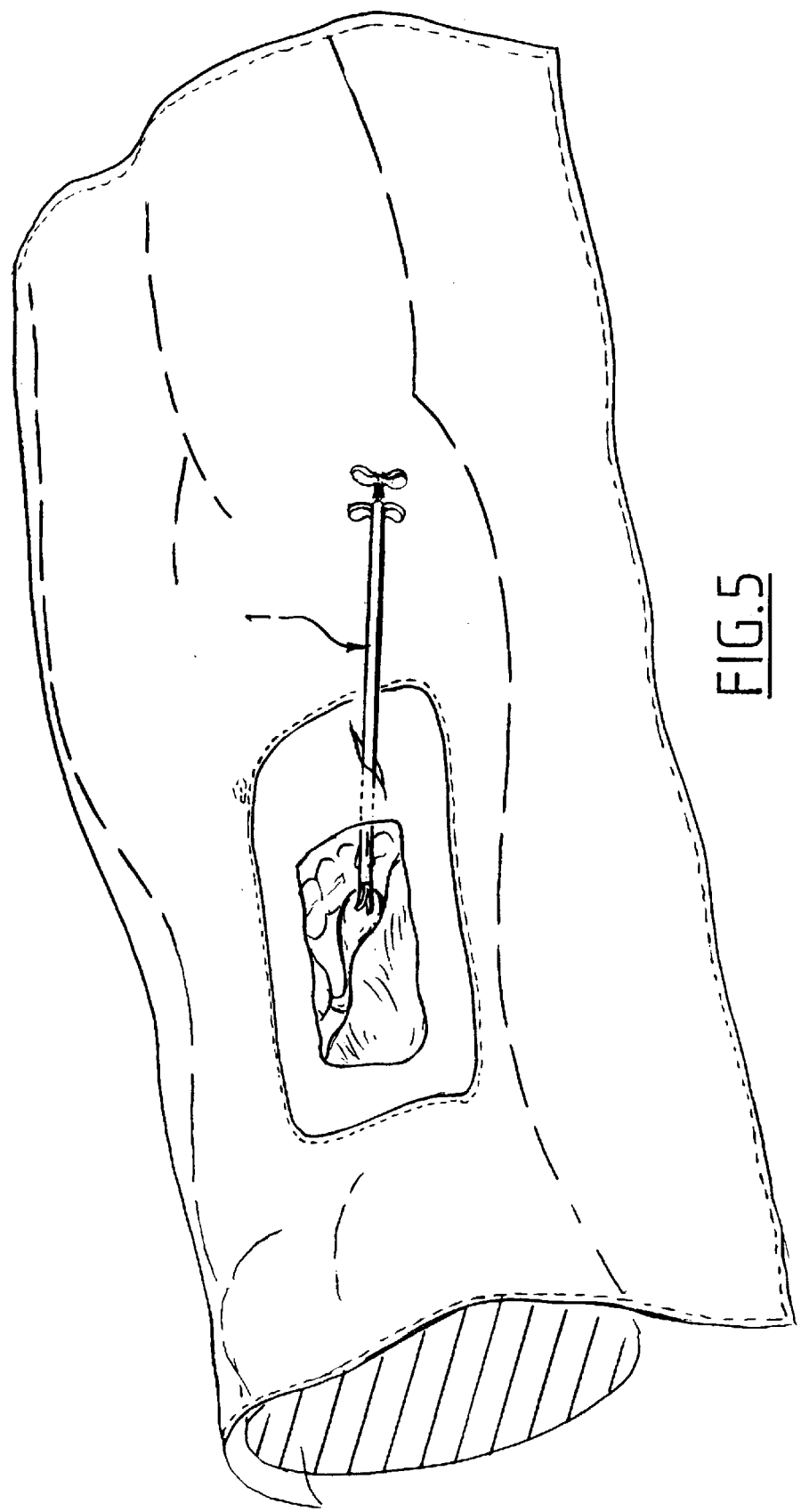

Further advantages, characteristics and details of the present invention will become clear with respect to the following description of a preferred embodiment thereof, which refers to the accompanying drawings in which are shown:

FIG. 1 a perspective view of the device according to the present invention;

FIG. 2 a shortened, perspective, partly cut away view of the device from FIG. 1, FIG. 3 a perspective, partially cut away view of a proximal part of the device from FIG. 1 and 2 during carrying out a severing action, FIG. 4 a perspective, partially cut away view of a proximal part of the device from FIGS. 1, 2 and 3, during the carrying out of a gripping action, and FIG. 5 a perspective view of the device from FIGS. 1 to 4 in use during a surgical operation.

The device 1 (FIG. 1) has a proximal part 2, a distal part 4 and a middle part 6 therebetween. Upper and lower finger grips 8 respectively 10 are mounted on an outer casing 12.

An upper thumb grip 14 and lower thumb grip 16 protrude from the casing 12 at the distal end 4.

Two beak elements 18, 20 are secured to the proximal part 2 of the device 1.

An upper rod 22, FIG. 2–4, extends from within the upper thumb grip 14 to terminate in a triangular part 24 thereof as shown in the figures.

A lower rod 26 extends from the lower thumb grip 16 through the casing 12 to terminate in an upward terminal section 28 thereof.

The upper and lower rods 22, 26 respectably, extend through a buffer plate 30 arranged near the distal end 4 of the device. An upper spring 32 extends around the upper rod 22 between the upper thumb grip 14 and the buffer plate 30.

A lower spring 34 extends around the lower rod 26 from the lower thumb grip 16 to the buffer plate 30.

An upper slot 36 extends diagonally in a forward direction from the back of the upper beak element 18, and a lower slot 38 extends diagonally, in the opposite direction to the upper slot 36, in the lower beak element 20. The terminal pin section 28 of the lower rod 26 extends through both of these slots 36, 38 respectably.

The upper beak element 18 is continuous with an upright flat section 40 thereof, which lies flat against a corresponding upright flat section 42 of the lower beak element 20.

An upwardly extending slot 44 extends from the rear of the flat section 40. A corresponding slot 46 also extends downwardly in the flat section 42. An end section 48 of the triangular part 24 of the upper rod 22 extends through these slots 44, 46 respectably.

A forwardly curved stabilizing pin 50 is arranged in the proximal end 2 of the casing 12 to extend through the upper end lower beak elements 18, 20 respectably.

A backwardly curved stabilizing pin 52 extends across the casing 12 transversely to the stabilizing pin 52, through the upright flat sections 40, 42 respectably.

The upper and lower beak elements 18, 20 respectably are provided with serrated edges 54, 56 respectably (see also FIGS. 3 and 4).

In order to sever tissue, the surgeon arranges his finger around the upper and lower finger grips 8, 10 and his thumb behind the lower thumb grip 16. On exerting force against the lower thumb grip 16, the lower rod 26 is pushed forward whereby the terminal pin section 28 thereof is pushed forward in the upper and lower slots 36, 38 of the upper and lower beak elements 18, 20, whereby due to the diagonally opposed nature of the slots, the upper and lower beak elements rotate in opposite directions about the stabilizing pin 50 to yield a scissor-like severing action. Control over the degree of severance is provided by the lower thumb grip being spring tensioned against the buffer plate 30 by means of the lower spring 34, FIG. 3.

During this motion, the upright flat sections 42, 40 are mutually displaced over the end section 48 of the triangular part 24 of upper rod 22.

In order to provide a forceps like gripping action the surgeon again arranges his fingers around the upper and lower finger grips, but this time exerts force on the upper thumb grip 14 in forward direction. On doing so the upper rod 22 is pushed in the direction of the distal end 2 of the device whereby the triangular end part 24 is pushed forward in the diagonally oppositely arranged slots 44, 46 of the upright flat sections 40, 42 of the beak elements 18, 20. On doing so, the upper and lower flat sections 40, 42 rotate about the stabilizing pin 52 in opposite directions so that the beak elements open and close in a jaw-like manner, FIG. 4. During this motion, the beak elements 18, 20 are mutually displaced over the stabilizing pin 50.

Control over this gripping action is enhanced by means of the gripping operation being spring tensioned due to the lower spring 34, and buffer-plate 30.

In order the yield good severance, the serrated edges of the beak elements do not extend across the whole severing surface thereof, whereby the severing surfaces remain substantially straight.

According to the present invention, the surgeon is therefore provided with one instrument which can perform both severing and gripping operations with a high degree of accuracy whereby a good deal of force can be exerted in both of these operations, substantially without detriment to the instrument itself, FIG. 5.

The present invention is not limited to the above described and illustrated embodiment, the requested rights are rather determined by the following claims.

What is claimed is:

1. A device for carrying out surgical operations comprising:

a distal part;

a middle part extending from the distal part;

a proximal part mounted on the middle part opposite to the distal part;

means for gripping body tissue and the like, which means are mounted near to the proximal part;

means near the proximal part of the device for severing body tissue;

means near the distal part of the device for operating the gripping means;

means near the distal part of the device for operating the severing means, the gripping means and the severing means comprise the same two co-operating elements, which preferably co-operate to form a beak-like unit; and one or both of the co-operating elements being displaceable in a first severing direction to provide a severing action, and one or both of the co-operating elements being also displaceable in a second gripping direction to provide a gripping action.

2. The device according to claim 1, wherein each element has a substantially flat part, and a substantially upright part connected thereto, wherein a first slot is arranged in the flat parts and wherein a second slot is arranged in the upright parts.

3. The device according to claim 2, wherein gripping transmission means extend through the first or second slots, and wherein severing transmission means extend through the second or first severing slots.

4. The device according to claim 1, wherein the gripping operating means comprise support means for the gripping means.

5. The device according to claim 6, wherein the gripping support means is moveable.

6. The device according to claim 1, wherein the severing operating means comprise support means for the severing means.

7. The device according to claim 6, wherein the severing support means is moveable.

8. The device according to claim 6, wherein the severing support means and the gripping support means are moveable with respect to each other.

9. The device according to claim 8, wherein the support means are substantially enclosed in a protective housing, which is preferably tubular in form.

* * * * *